(12) United States Patent
Goodwin et al.

(10) Patent No.: US 8,133,976 B2
(45) Date of Patent: Mar. 13, 2012

(54) METHODS OF USE OF THE TACI/TACI-L INTERACTION

(75) Inventors: Raymond G. Goodwin, Seattle, WA (US); Wanwan S. Din, Issaquah, WA (US)

(73) Assignee: Immunex Corporation, Thousand Oaks, CA (US)

( * ) Notice: Subject to any disclaimer, the term of this patent is extended or adjusted under 35 U.S.C. 154(b) by 0 days.

(21) Appl. No.: 12/614,109

(22) Filed: Nov. 6, 2009

(65) Prior Publication Data

US 2010/0196404 A1 Aug. 5, 2010

Related U.S. Application Data

(63) Continuation of application No. 12/220,483, filed on Jul. 23, 2008, now abandoned, which is a continuation of application No. 09/302,863, filed on Apr. 30, 1999, now abandoned.

(51) Int. Cl.
*C07K 14/525* (2006.01)
*C07K 14/475* (2006.01)
*C07K 14/715* (2006.01)

(52) U.S. Cl. ........................................ 530/351; 930/140
(58) Field of Classification Search ........................ None
See application file for complete search history.

(56) References Cited

U.S. PATENT DOCUMENTS

| | | | |
|---|---|---|---|
| 4,959,457 A | 9/1990 | Bringman | |
| 5,340,716 A | 8/1994 | Ullman et al. | |
| 5,525,708 A | 6/1996 | Nocka et al. | |
| 5,932,540 A | 8/1999 | Hu et al. | |
| 5,969,102 A | 10/1999 | Bram et al. | |
| 6,316,222 B1 | 11/2001 | Bram et al. | |
| 2003/0199020 A1* | 10/2003 | Fitzpatrick et al. | 435/69.1 |
| 2006/0067933 A1 | 3/2006 | Gross et al. | |

FOREIGN PATENT DOCUMENTS

| | | |
|---|---|---|
| EP | 0869180 A1 | 7/1998 |
| EP | 0911633 A1 | 4/1999 |
| EP | 0919620 A3 | 8/1999 |
| WO | WO 96/34095 | 10/1996 |
| WO | WO 97/33902 | 9/1997 |
| WO | WO 98/18921 | 5/1998 |
| WO | WO 98/27114 | 6/1998 |
| WO | WO 98/39361 | 9/1998 |
| WO | WO 98/55620 | 12/1998 |
| WO | WO 98/55621 | 12/1998 |
| WO | WO 99/11791 | 3/1999 |
| WO | WO 99/12964 | 3/1999 |
| WO | WO 99/12965 | 3/1999 |
| WO | WO 99/28462 | 6/1999 |
| WO | WO 99/33980 | 7/1999 |
| WO | WO 99/35170 | 7/1999 |
| WO | WO 00/40716 | 7/2000 |
| WO | WO 00/68378 | 11/2000 |

OTHER PUBLICATIONS

Alberts, Bruce, Molecular biology of the cell, New York: Garland Pub., c1983, pp. 264-266.
Bowie et al., "Deciphering the message in protein sequences: tolerance to amino acid substitutions," *Science*, 247(4948):1306-1310, 1990.
Creighton, T. E., Proteins: Structures and Molecular Properties. W.H. Freeman, New York. pp. 335-339, 1984.
Gross et al., U.S. Appl. No. 60/115,068, filed Jan. 7, 1999.
Khare, S. et al., "Severe B cell hyperplasia and autoimmune disease in TALL-1 transgenic mice," *PNAS* 97(7):3370-3375, 2000.
Moore, P., et al., "BlyS: Member of the tumor necrosis factor family and B lymphocyte stimulator," *Science* 285: 260-263, 1999.
Mukhopadhyay, A., et al., "Identification and characterization of a novel cytokine, THANK, a TNF homologue that activates apoptosis, nuclear factor-κB, and c-Jun NH$_2$-terminal kinase," *J. Biol. Chem.* 274(23): 15978-15981, 1999.
Ngo et al., In the Protein Folding Problem and Tertiary Structure Prediction, Merz and Le Grand (Eds), Aug. 1994, Springer Verlag, pp. 433 and 492-495.
Schneider, P., et al., "BAFF, a novel ligand of the tumor necrosis factor family, stimulates B cell growth," *J. Exp. Med.* 189(11): 1747-1756, 1999.
Shu, H., et al., "TALL-1 is a novel member of the TNF family that is down-regulated by mitogens," *J. Leuk. Biol.* 65: 680-683, 1999.
Von Bulow, G., et al., "NF-AT Activation Induced by a CAML-Interacting Member of the Tumor Necrosis Factor Receptor Superfamily," *Science* 278: 138-141, 1997.
Wells, J. A., Additivity of mutational effects in proteins, *Biochem.*, 29(37):8509-8517, 1990.

* cited by examiner

*Primary Examiner* — David Romeo
(74) *Attorney, Agent, or Firm* — James E. Klaniecki (57) ABSTRACT

The invention discloses a novel interaction between a TNF receptor (TACI) and its interacting ligand (TACI-L). Also disclosed are methods of screening candidate molecules to determine potential antagonists and agonists of the TACI/TACI-L interaction. The use of the antagonists and agonists as therapeutics to treat autoimmune diseases, inflammation, and to inhibit graft vs. host rejections is further disclosed.

1 Claim, 7 Drawing Sheets

| | |
|---|---|
| AGCATCCTGA GTAATGAGTG GCCTGGGCCG GAGCAGGCGA GGTGGCCGGA GCCGTGTGGA | 60 |
| CCAGGAGGAG CGCTTTCCAC AGGGCCTGTG GACGGGGGTG GCTATGAGAT CCTGCCCCGA | 120 |
| AGAGCAGTAC TGGGATCCTC TGCTGGGTAC CTGCATGTCC TGCAAAACCA TTTGCAACCA | 180 |
| TCAGAGCCAG CGCACCTGTG CAGCCTTCTG CAGGTCACTC AGCTGCCGCA AGGAGCAAGG | 240 |
| CAAGTTCTAT GACCATCTCC TGAGGGACTG CATCAGCTGT GCCTCCATCT GTGGACAGCA | 300 |
| CCCTAAGCAA TGTGCATACT TCTGTGAGAA CAAGCTCAGG AGCCCAGTGA ACCTTCCACC | 360 |
| AGAGCTCAGG AGACAGCGGA GTGGAGAAGT TGAAAACAAT TCAGACAACT CGGGAAGGTA | 420 |
| CCAAGGATTG GAGCACAGAG GCTCAGAAGC AAGTCCAGCT CTCCCGGGGC TGAAGCTGAG | 480 |
| TGCAGATCAG GTGGCCCTGG TCTACAGCAC GCTGGGGCTC TGCCTGTGTG CCGTCCTCTG | 540 |
| CTGCTTCCTG GTGGCGGTGG CCTGCTTCCT CAAGAAGAGG GGGGATCCCT GCTCCTGCCA | 600 |
| GCCCCGCTCA AGGCCCCGTC AAAGTCCGGC CAAGTCTTCC CAGGATCACG CGATGGAAGC | 660 |
| CGGCAGCCCT GTGAGCACAT CCCCCGAGCC AGTGGAGACC TGCAGCTTCT GCTTCCCTGA | 720 |
| GTGCAGGGCG CCCACGCAGG AGAGCGCAGT CACGCCTGGG ACCCCCGACC CCACTTGTGC | 780 |
| TGGAAGGTGG GGGTGCCACA CCAGGACCAC AGTCCTGCAG CCTTGCCCAC ACATCCCAGA | 840 |
| CAGTGGCCTT GGCATTGTGT GTGTGCCTGC CCAGGAGGGG GGCCCAGGTG CATAAATGGG | 900 |
| GGTCAGGGAG GGAAAGGAGG AGGGAGAGAG ATGGAGAGGA GGGGAGAGAG AAAGAGAGGT | 960 |
| GGGGAGAGGG GAGAGAGATA TGAGGAGAGA GAGACAGAGG AGGCAGAAAG GGAGAGAAAC | 1020 |
| AGAGGAGACA GAGAGGGAGA GAGAGACAGA GGGAGAGAGA GACAGAGGGG AAGAGAGGCA | 1080 |
| GAGAGGGAAA GAGGCAGAGA AGGAAAGAGA CAGGCAGAGA AGGAGAGAGG CAGAGAGGGA | 1140 |
| GAGAGGCAGA GAGGGAGAGA GGCAGAGAGA CAGAGAGGGA GAGAGGGACA GAGAGAGATA | 1200 |
| GAGCAGGAGG TCGGGGCACT CTGAGTCCCA GTTCCCAGTG CAGCTGTAGG TCGTCATCAC | 1260 |
| CTAACCACAC GTGCAATAAA GTCCTCGTGC CTGCTGCTCA CAGCCCCCGA GAGCCCCTCC | 1320 |
| TCCTGGAGAA TAAAACCTTT GGCAGCTGCC CTTCCTCAAA AAAAAAAAAA AAAAAA | 1377 |

*Fig. 1A*

Met Ser Gly Leu Gly Arg Ser Arg Arg Gly Gly Arg Ser Arg Val Asp
1          5                   10                  15
Gln Glu Glu Arg Phe Pro Gln Gly Leu Trp Thr Gly Val Ala Met Arg
            20              25                  30
Ser Cys Pro Glu Glu Gln Tyr Trp Asp Pro Lue Leu Gly Thr Cys Met
        35              40              45
Ser Cys Lys Thr Ile Cys Asn His Gln Ser Gln Arg Thr Cys Ala Ala
    50              55                  60
Phe Cys Arg Ser Leu Ser Cys Arg Lys Glu Gln Gly Lys Phe Tyr Asp
65              70              75                          80
His Leu Leu Arg Asp Cys Ile Ser Cys Ala Ser Ile Cys Gly Gln His
                85              90              95
Pro Lys Gln Cys Ala Tyr Phe Cys Glu Asn Lys Leu Arg Ser Pro Val
            100             105                 110
Asn Leu Pro Pro Glu Leu Arg Arg Gln Arg Ser Gly Glu Val Glu Asn
        115             120                 125
Asn Ser Asp Asn Ser Gly Arg Tyr Gln Gly Leu Glu His Arg Gly Ser
    130             135                 140
Glu Ala Ser Pro Ala Leu Pro Gly Leu Lys Leu Ser Ala Asp Gln Val
145             150                 155                     160
Ala Leu Val Tyr Ser Thr Leu Gly Leu Cys Leu Cys Ala Val Leu Cys
            165                 170                 175
Cys Phe Leu Val Ala Val Ala Cys Phe Leu Lys Lys Arg Gly Asp Pro
            180                 185                 190
Cys Ser Cys Gln Pro Arg Ser Arg Pro Arg Gln Ser Pro Ala Lys Ser
        195                 200                 205
Ser Gln Asp His Ala Met Glu Ala Gly Ser Pro Val Ser Thr Ser Pro
    210                 215                 220
Glu Pro Val Glu Thr Cys Ser Phe Cys Phe Pro Glu Cys Arg Ala Pro
225                 230                 235                 240
Thr Gln Glu Ser Ala Val Thr Pro Gly Thr Pro Asp Pro Thr Cys Ala
            245                 250                 255
Gly Arg Trp Gly Cys His Thr Arg Thr Thr Val Leu Gln Pro Cys Pro
            260                 265                 270
His Ile Pro Asp Ser Gly Leu Gly Ile Val Cys Val Pro Ala Gln Glu
        275                 280                 285
Gly Gly Pro Gly Ala
        290

*Fig. 1B*

(START AND STOP CODONS ARE IN BOLD TYPE)

AGCAAGTTCA GCCTGGTTAA GTCCAAGCTG AATTCCGGTC AAAGTTCAAG
TAGTGATATG GATGACTCCA CAGAAAGGGA GCAGTCACGC CTTACTTCTT
GCCTTAAGAA AAGAGAAGAA ATGAAACTGA AGGAGTGTGT TTCCATCCTC
CCACGGAAGG AAAGCCCCTC TGTCCGATCC TCCAAAGACG GAAAGCTGCT
GGCTGCAACC TTGCTGCTGG CACTGCTGTC TTGCTGCCTC ACGGTGGTGT
CTTTCTACCA GGTGGCCGCC CTGCAAGGGG ACCTGGCCAG CCTCCGGGCA
GAGCTGCAGG GCCACCACGC GGAGAAGCTG CCAGCAGGAG CAGGAGCCCC
CAAGGCCGGC CTGGAGGAAG CTCCAGCTGT CACCGCGGGA CTGAAAATCT
TTGAACCACC AGCTCCAGGA GAAGGCAACT CCAGTCAGAA CAGCAGAAAT
AAGCGTGCCG TTCAGGGTCC AGAAGAAACA GTCACTCAAG ACTGCTTGCA
ACTGATTGCA GACAGTGAAA CACCAACTAT ACAAAAGGA TCTTACACAT
TTGTTCCATG GCTTCTCAGC TTTAAAAGGG GAAGTGCCCT AGAAGAAAAA
GAGAATAAAA TATTGGTCAA AGAAACTGGT TACTTTTTTA TATATGGTCA
GGTTTTATAT ACTGATAAGA CCTACGCCAT GGGACATCTA ATTCAGAGGA
AGAAGGTCCA TGTCTTTGGG GATGAATTGA GTCTGGTGAC TTTGTTTCGA
TGTATTCAAA ATATGCCTGA AACACTACCC AATAATTCCT GCTATTCAGC
TGGCATTGCA AAACTGGAAG AAGGAGATGA ACTCCAACTT GCAATACCAA
GAGAAAATGC ACAAATATCA CTGGATGGAG ATGTCACATT TTTTGGTGCA
TTGAAACTGC TGTGACCTAC TTACACCATG TCTGTAGCTA TTTTCCTCCC
TTTCTCTGTA CCTCTAAGAA GAAAGAATCT AACTGAAAAT ACCAAAAAAA
AAAAAAAAAA AAAAAGATCT TTAATTAAGC GGCCGCAAGC TTATTCCCTT
TAGTGAG

*Fig. 2A*

TRANSLATION IN RELEVANT READING FRAME (3' 5'):

MDDSTEREQS RLTSCLKKRE EMKLKECVSI LPRKESPSVR SSKDGKLLAA
TLLLALLSCC LTVVSFYQVA ALQGDLASLR AELQGHHAEK LPAGAGAPKA
GLEEAPAVTA GLKIFEPPAP GEGNSSQNSR NKRAVQGPEE TVTQDCLQLI
ADSETPTIQK GSYTFVPWLL SFKRGSALEE KENKILVKET GYFFIYGQVL
YTDKTYAMGH LIQRKKVHVF GDELSLVTLF RCIQNMPETL PNNSCYSAGI
AKLEEGDELQ LAIPRENAQI SLDGDVTFFG ALKLL

*Fig. 2B*

TRANSLATION IN RELEVANT READING FRAME (3' 5'):

MARRLWILSL LAVTLTVALA APSQKSKRRT SSDRMKQIED KIEEILSKIY
HIENEIARIK KLIGERTRSG NSSQNSRNKR AVQGPEETVT QDCLQLIADS
ETPTIQKGSY TFVPWLLSFK RGSALEEKEN KILVKETGYF FIYGQVLYTD
KTYAMGHLIQ RKKVHVFGDE LSLVTLFRCI QNMPETLPNN SCYSAGIAKL
EEGDELQLAI PRENAQISLD GDVTFFGALK LL
(SEQ ID NO:3)

□ BOUND/FREE
—— $-1.536779e+09*X +1.884189e+13$

□ BOUND/FREE
——— −2.169997e+09*X +3.374496e+13

SEQUENCE LISTING

<160> NUMBER OF SEQ ID NOS: 5

<210> SEQ ID NO 1
<211> LENGTH: 1377
<212> TYPE: DNA
<213> ORGANISM: Human
<220> FEATURE:
<221> NAME/KEY: CDS
<222> LOCATION: (14)..(892)

<400> SEQUENCE: 1

```
agcatcctga gta atg agt ggc ctg ggc cgg agc agg cga ggt ggc cgg         49
            Met Ser Gly Leu Gly Arg Ser Arg Arg Gly Gly Arg
             1               5                  10 agc cgt gtg gac cag gag gag cgc ttt cca cag ggc ctg tgg acg ggg        97
Ser Arg Val Asp Gln Glu Glu Arg Phe Pro Gln Gly Leu Trp Thr Gly
        15                  20                  25 gtg gct atg aga tcc tgc ccc gaa gag cag tac tgg gat cct ctg ctg       145
Val Ala Met Arg Ser Cys Pro Glu Glu Gln Tyr Trp Asp Pro Leu Leu
    30                  35                  40 ggt acc tgc atg tcc tgc aaa acc att tgc aac cat cag agc cag cgc       193
Gly Thr Cys Met Ser Cys Lys Thr Ile Cys Asn His Gln Ser Gln Arg
45                  50                  55                  60 acc tgt gca gcc ttc tgc agg tca ctc agc tgc cgc aag gag caa ggc       241
Thr Cys Ala Ala Phe Cys Arg Ser Leu Ser Cys Arg Lys Glu Gln Gly
                65                  70                  75 aag ttc tat gac cat ctc ctg agg gac tgc atc agc tgt gcc tcc atc       289
Lys Phe Tyr Asp His Leu Leu Arg Asp Cys Ile Ser Cys Ala Ser Ile
            80                  85                  90 tgt gga cag cac cct aag caa tgt gca tac ttc tgt gag aac aag ctc       337
Cys Gly Gln His Pro Lys Gln Cys Ala Tyr Phe Cys Glu Asn Lys Leu
        95                 100                 105 agg agc cca gtg aac ctt cca cca gag ctc agg aga cag cgg agt gga       385
Arg Ser Pro Val Asn Leu Pro Pro Glu Leu Arg Arg Gln Arg Ser Gly
    110                 115                 120 gaa gtt gaa aac aat tca gac aac tcg gga agg tac caa gga ttg gag       433
Glu Val Glu Asn Asn Ser Asp Asn Ser Gly Arg Tyr Gln Gly Leu Glu
125                 130                 135                 140 cac aga ggc tca gaa gca agt cca gct ctc ccg ggg ctg aag ctg agt       481
His Arg Gly Ser Glu Ala Ser Pro Ala Leu Pro Gly Leu Lys Leu Ser
                145                 150                 155 gca gat cag gtg gcc ctg gtc tac agc acg ctg ggg ctc tgc ctg tgt       529
Ala Asp Gln Val Ala Leu Val Tyr Ser Thr Leu Gly Leu Cys Leu Cys
            160                 165                 170
```

| | | | | | | | | | | | | | | | |
|---|---|---|---|---|---|---|---|---|---|---|---|---|---|---|---|
| gcc | gtc | ctc | tgc | tgc | ttc | ctg | gtg | gcg | gtg | gcc | tgc | ttc | ctc | aag aag | 577 |
| Ala | Val | Leu | Cys | Cys | Phe | Leu | Val | Ala | Val | Ala | Cys | Phe | Leu | Lys Lys | |
| | | 175 | | | | | 180 | | | | | 185 | | | |
| agg | ggg | gat | ccc | tgc | tcc | tgc | cag | ccc | cgc | tca | agg | ccc | cgt | caa agt | 625 |
| Arg | Gly | Asp | Pro | Cys | Ser | Cys | Gln | Pro | Arg | Ser | Arg | Pro | Arg | Gln Ser | |
| | | 190 | | | | | 195 | | | | | 200 | | | |
| ccg | gcc | aag | tct | tcc | cag | gat | cac | gcg | atg | gaa | gcc | ggc | agc | cct gtg | 673 |
| Pro | Ala | Lys | Ser | Ser | Gln | Asp | His | Ala | Met | Glu | Ala | Gly | Ser | Pro Val | |
| 205 | | | | | 210 | | | | | 215 | | | | | 220 |
| agc | aca | tcc | ccc | gag | cca | gtg | gag | acc | tgc | agc | ttc | tgc | ttc | cct gag | 721 |
| Ser | Thr | Ser | Pro | Glu | Pro | Val | Glu | Thr | Cys | Ser | Phe | Cys | Phe | Pro Glu | |
| | | | | 225 | | | | | 230 | | | | | 235 | |
| tgc | agg | gcg | ccc | acg | cag | gag | agc | gca | gtc | acg | cct | ggg | acc | ccc gac | 769 |
| Cys | Arg | Ala | Pro | Thr | Gln | Glu | Ser | Ala | Val | Thr | Pro | Gly | Thr | Pro Asp | |
| | | | 240 | | | | | 245 | | | | | 250 | | |
| ccc | act | tgt | gct | gga | agg | tgg | ggg | tgc | cac | acc | agg | acc | aca | gtc ctg | 817 |
| Pro | Thr | Cys | Ala | Gly | Arg | Trp | Gly | Cys | His | Thr | Arg | Thr | Thr | Val Leu | |
| | | | | 255 | | | | | 260 | | | | | 265 | |
| cag | cct | tgc | cca | cac | atc | cca | gac | agt | ggc | ctt | ggc | att | gtg | tgt gtg | 865 |
| Gln | Pro | Cys | Pro | His | Ile | Pro | Asp | Ser | Gly | Leu | Gly | Ile | Val | Cys Val | |
| | | 270 | | | | | 275 | | | | | 280 | | | |
| cct | gcc | cag | gag | ggg | ggc | cca | ggt | gca | taaatggggg | | tcagggaggg | | | | 912 |
| Pro | Ala | Gln | Glu | Gly | Gly | Pro | Gly | Ala | | | | | | | |
| 285 | | | | | 290 | | | | | | | | | | |

```
aaaggaggag ggagagagat ggagaggagg ggagagagaa agagaggtgg ggagagggga   972
gagagatatg aggagagaga gacagaggag gcagaaaggg agagaaacag aggagacaga  1032
gagggagaga gagacagagg gagagagaga cagagggaga gagaggcaga gagggaaaga  1092
ggcagagaag gaaagagaca ggcagagaag gagagaggca gagagggaga gaggcagaga  1152
gggagagagg cagagagaca gagagggaga gagggacaga gagagataga gcaggaggtc  1212
ggggcactct gagtcccagt tcccagtgca gctgtaggtc gtcatccct aaccacacgt   1272
gcaataaagt cctcgtgcct gctgctcaca gcccccgaga gcccctcctc ctggagaata  1332
aaacctttgg cagctgccct tcctcaaaaa aaaaaaaaaa aaaaa              1377
```

<210> SEQ ID NO 2
<211> LENGTH: 293
<212> TYPE: PRT
<213> ORGANISM: Human

<400> SEQUENCE: 2

Met Ser Gly Leu Gly Arg Ser Arg Arg Gly Gly Arg Ser Arg Val Asp
 1               5                  10                  15

Gln Glu Glu Arg Phe Pro Gln Gly Leu Trp Thr Gly Val Ala Met Arg
                20                  25                  30

Ser Cys Pro Glu Glu Gln Tyr Trp Asp Pro Leu Leu Gly Thr Cys Met
             35                  40                  45

Ser Cys Lys Thr Ile Cys Asn His Gln Ser Gln Arg Thr Cys Ala Ala
         50                  55                  60

Phe Cys Arg Ser Leu Ser Cys Arg Lys Glu Gln Gly Lys Phe Tyr Asp
 65                  70                  75                  80

His Leu Leu Arg Asp Cys Ile Ser Cys Ala Ser Ile Cys Gly Gln His
                 85                  90                  95

Pro Lys Gln Cys Ala Tyr Phe Cys Glu Asn Lys Leu Arg Ser Pro Val
            100                 105                 110

Asn Leu Pro Pro Glu Leu Arg Arg Gln Arg Ser Gly Glu Val Glu Asn
        115                 120                 125

```
Asn Ser Asp Asn Ser Gly Arg Tyr Gln Gly Leu Glu His Arg Gly Ser
        130                 135                 140
Glu Ala Ser Pro Ala Leu Pro Gly Leu Lys Leu Ser Ala Asp Gln Val
145                 150                 155                 160
Ala Leu Val Tyr Ser Thr Leu Gly Leu Cys Leu Cys Ala Val Leu Cys
                165                 170                 175
Cys Phe Leu Val Ala Val Ala Cys Phe Leu Lys Lys Arg Gly Asp Pro
            180                 185                 190
Cys Ser Cys Gln Pro Arg Ser Arg Pro Arg Gln Ser Pro Ala Lys Ser
        195                 200                 205
Ser Gln Asp His Ala Met Glu Ala Gly Ser Pro Val Ser Thr Ser Pro
    210                 215                 220
Glu Pro Val Glu Thr Cys Ser Phe Cys Phe Pro Glu Cys Arg Ala Pro
225                 230                 235                 240
Thr Gln Glu Ser Ala Val Thr Pro Gly Thr Pro Asp Pro Thr Cys Ala
                245                 250                 255
Gly Arg Trp Gly Cys His Thr Arg Thr Thr Val Leu Gln Pro Cys Pro
            260                 265                 270
His Ile Pro Asp Ser Gly Leu Gly Ile Val Cys Val Pro Ala Gln Glu
        275                 280                 285
Gly Gly Pro Gly Ala
    290

<210> SEQ ID NO 3
<211> LENGTH: 1057
<212> TYPE: DNA
<213> ORGANISM: Human
<220> FEATURE:
<221> NAME/KEY: CDS
<222> LOCATION: (58)..(912)

<400> SEQUENCE: 3
agcaagttca gcctggttaa gtccaagctg aattccggtc aaagttcaag tagtgat          57 atg gat gac tcc aca gaa agg gag cag tca cgc ctt act tct tgc ctt       105
Met Asp Asp Ser Thr Glu Arg Glu Gln Ser Arg Leu Thr Ser Cys Leu
1               5                   10                  15 aag aaa aga gaa gaa atg aaa ctg aag gag tgt gtt tcc atc ctc cca       153
Lys Lys Arg Glu Glu Met Lys Leu Lys Glu Cys Val Ser Ile Leu Pro
            20                  25                  30 cgg aag gaa agc ccc tct gtc cga tcc tcc aaa gac gga aag ctg ctg       201
Arg Lys Glu Ser Pro Ser Val Arg Ser Ser Lys Asp Gly Lys Leu Leu
        35                  40                  45 gct gca acc ttg ctg ctg gca ctg ctg tct tgc tgc ctc acg gtg gtg       249
Ala Ala Thr Leu Leu Leu Ala Leu Leu Ser Cys Cys Leu Thr Val Val
    50                  55                  60 tct ttc tac cag gtg gcc gcc ctg caa ggg gac ctg gcc agc ctc cgg       297
Ser Phe Tyr Gln Val Ala Ala Leu Gln Gly Asp Leu Ala Ser Leu Arg
65                  70                  75                  80 gca gag ctg cag ggc cac cac gcg gag aag ctg cca gca gga gca gga       345
Ala Glu Leu Gln Gly His His Ala Glu Lys Leu Pro Ala Gly Ala Gly
                85                  90                  95 gcc ccc aag gcc ggc ctg gag gaa gct cca gct gtc acc gcg gga ctg       393
Ala Pro Lys Ala Gly Leu Glu Glu Ala Pro Ala Val Thr Ala Gly Leu
            100                 105                 110 aaa atc ttt gaa cca cca gct cca gga gaa ggc aac tcc agt cag aac       441
Lys Ile Phe Glu Pro Pro Ala Pro Gly Glu Gly Asn Ser Ser Gln Asn
        115                 120                 125 agc aga aat aag cgt gcc gtt cag ggt cca gaa gaa aca gtc act caa       489
Ser Arg Asn Lys Arg Ala Val Gln Gly Pro Glu Glu Thr Val Thr Gln
```

```
             130                 135                 140
gac tgc ttg caa ctg att gca gac agt gaa aca cca act ata caa aaa      537
Asp Cys Leu Gln Leu Ile Ala Asp Ser Glu Thr Pro Thr Ile Gln Lys
145                 150                 155                 160 gga tct tac aca ttt gtt cca tgg ctt ctc agc ttt aaa agg gga agt      585
Gly Ser Tyr Thr Phe Val Pro Trp Leu Leu Ser Phe Lys Arg Gly Ser
                165                 170                 175 gcc cta gaa gaa aaa gag aat aaa ata ttg gtc aaa gaa act ggt tac      633
Ala Leu Glu Glu Lys Glu Asn Lys Ile Leu Val Lys Glu Thr Gly Tyr
            180                 185                 190 ttt ttt ata tat ggt cag gtt tta tat act gat aag acc tac gcc atg      681
Phe Phe Ile Tyr Gly Gln Val Leu Tyr Thr Asp Lys Thr Tyr Ala Met
        195                 200                 205 gga cat cta att cag agg aag aag gtc cat gtc ttt ggg gat gaa ttg      729
Gly His Leu Ile Gln Arg Lys Lys Val His Val Phe Gly Asp Glu Leu
    210                 215                 220 agt ctg gtg act ttg ttt cga tgt att caa aat atg cct gaa aca cta      777
Ser Leu Val Thr Leu Phe Arg Cys Ile Gln Asn Met Pro Glu Thr Leu
225                 230                 235                 240 ccc aat aat tcc tgc tat tca gct ggc att gca aaa ctg gaa gaa gga      825
Pro Asn Asn Ser Cys Tyr Ser Ala Gly Ile Ala Lys Leu Glu Glu Gly
                245                 250                 255 gat gaa ctc caa ctt gca ata cca aga gaa aat gca caa ata tca ctg      873
Asp Glu Leu Gln Leu Ala Ile Pro Arg Glu Asn Ala Gln Ile Ser Leu
            260                 265                 270 gat gga gat gtc aca ttt ttt ggt gca ttg aaa ctg ctg tgacctactt      922
Asp Gly Asp Val Thr Phe Phe Gly Ala Leu Lys Leu Leu
        275                 280                 285 acaccatgtc tgtagctatt ttcctcccctt tctctgtacc tctaagaaga aagaatctaa    982
ctgaaaatac caaaaaaaaa aaaaaaaaaa aaagatcttt aattaagcgg ccgcaagctt   1042
attcccttta gtgag                                                    1057

<210> SEQ ID NO 4
<211> LENGTH: 285
<212> TYPE: PRT
<213> ORGANISM: Human

<400> SEQUENCE: 4

Met Asp Asp Ser Thr Glu Arg Glu Gln Ser Arg Leu Thr Ser Cys Leu
1               5                   10                  15

Lys Lys Arg Glu Glu Met Lys Leu Lys Glu Cys Val Ser Ile Leu Pro
            20                  25                  30

Arg Lys Glu Ser Pro Ser Val Arg Ser Ser Lys Asp Gly Lys Leu Leu
        35                  40                  45

Ala Ala Thr Leu Leu Ala Leu Leu Ser Cys Cys Leu Thr Val Val
    50                  55                  60

Ser Phe Tyr Gln Val Ala Ala Leu Gln Gly Asp Leu Ala Ser Leu Arg
65                  70                  75                  80

Ala Glu Leu Gln Gly His His Ala Glu Lys Leu Pro Ala Gly Ala Gly
                85                  90                  95

Ala Pro Lys Ala Gly Leu Glu Glu Ala Pro Ala Val Thr Ala Gly Leu
            100                 105                 110

Lys Ile Phe Glu Pro Pro Ala Pro Gly Glu Gly Asn Ser Ser Gln Asn
        115                 120                 125

Ser Arg Asn Lys Arg Ala Val Gln Gly Pro Glu Glu Thr Val Thr Gln
    130                 135                 140

Asp Cys Leu Gln Leu Ile Ala Asp Ser Glu Thr Pro Thr Ile Gln Lys
```

```
                145                 150                 155                 160
Gly Ser Tyr Thr Phe Val Pro Trp Leu Leu Ser Phe Lys Arg Gly Ser
                    165                 170                 175
Ala Leu Glu Glu Lys Glu Asn Lys Ile Leu Val Lys Glu Thr Gly Tyr
                180                 185                 190
Phe Phe Ile Tyr Gly Gln Val Leu Tyr Thr Asp Lys Thr Tyr Ala Met
            195                 200                 205
Gly His Leu Ile Gln Arg Lys Val His Val Phe Gly Asp Glu Leu
        210                 215                 220
Ser Leu Val Thr Leu Phe Arg Cys Ile Gln Asn Met Pro Glu Thr Leu
225                 230                 235                 240
Pro Asn Asn Ser Cys Tyr Ser Ala Gly Ile Ala Lys Leu Glu Glu Gly
                245                 250                 255
Asp Glu Leu Gln Leu Ala Ile Pro Arg Glu Asn Ala Gln Ile Ser Leu
            260                 265                 270
Asp Gly Asp Val Thr Phe Phe Gly Ala Leu Lys Leu Leu
        275                 280                 285

<210> SEQ ID NO 5
<211> LENGTH: 232
<212> TYPE: PRT
<213> ORGANISM: human

<400> SEQUENCE: 5

Met Ala Arg Arg Leu Trp Ile Leu Ser Leu Leu Ala Val Thr Leu Thr
1               5                   10                  15
Val Ala Leu Ala Ala Pro Ser Lys Ser Lys Arg Arg Thr Ser Ser Asp
                20                  25                  30
Arg Met Lys Gln Ile Glu Asp Lys Ile Glu Glu Ile Leu Ser Lys Ile
            35                  40                  45
Tyr His Ile Glu Asn Glu Ile Ala Arg Ile Lys Lys Leu Ile Gly Glu
        50                  55                  60
Arg Thr Arg Ser Gly Asn Ser Ser Gln Asn Ser Arg Asn Lys Arg Ala
65                  70                  75                  80
Val Gln Gly Pro Glu Glu Thr Val Thr Gln Asp Cys Leu Gln Leu Ile
                85                  90                  95
Ala Asp Ser Glu Thr Pro Thr Ile Gln Lys Gly Ser Tyr Thr Phe Val
            100                 105                 110
Pro Trp Leu Leu Ser Phe Lys Arg Gly Ser Ala Leu Glu Glu Lys Glu
        115                 120                 125
Asn Lys Ile Leu Val Lys Glu Thr Gly Tyr Phe Phe Ile Tyr Gly Gln
    130                 135                 140
Val Leu Tyr Thr Asp Lys Thr Tyr Ala Met Gly His Leu Ile Gln Arg
145                 150                 155                 160
Lys Lys Val His Val Phe Gly Asp Glu Leu Ser Leu Val Thr Leu Phe
                165                 170                 175
Arg Ile Cys Ile Gln Asn Met Pro Glu Thr Leu Pro Asn Asn Ser Cys
            180                 185                 190
Tyr Ser Ala Gly Ile Ala Lys Leu Glu Glu Gly Asp Glu Leu Gln Leu
        195                 200                 205
Ala Thr Pro Arg Glu Asn Ala Gln Ile Ser Leu Asp Gly Asp Val Thr
    210                 215                 220
Phe Phe Gly Ala Leu Lys Leu Leu
225                 230
```

METHODS OF USE OF THE TACI/TACI-L INTERACTION

CROSS-REFERENCE TO RELATED APPLICATIONS

This application is a continuation of U.S. patent application Ser. No. 12/220,483, filed Jul. 23, 2008, which is a continuation of U.S. patent application Ser. No. 09/302,863, filed Apr. 30, 1999, which is incorporated herein by reference.

FIELD OF INVENTION

This invention relates generally to the interaction between the transmembrane activator and CAML-interactor (TACI) protein and its ligand, TACI ligand (TACI-L), use of the interaction in screening assays thereof, and related kits.

BACKGROUND OF THE INVENTION

Cellular change is often triggered by the binding of an extrinsic element, such as a ligand, to the extracellular domain of a cell surface membrane receptor protein. This binding can result in cellular changes by activating and controlling intracellular signaling cascades and cell regulatory mechanisms. As such, understanding the initial binding interaction between the ligand and its receptor protein can be of great interest to the scientific community. A greater understanding of this interaction would enable one skilled in the art to modulate the resulting signaling cascade governed by the ligand/receptor interaction by selecting agents for co-stimulation or inhibition of the binding of the ligand to its receptor.

The tumor necrosis factor (TNF) receptor family is a class of mammalian signaling molecules that play an important role in protection against infection and immune inflammatory responses such as cellular signal transduction, stimulation of cells to secrete cytokines, cytotoxic T cell proliferation, general cellular proliferation, lymph node formation, bone formation, and bone degradation. TNF-mediated cellular signaling often involves a molecular activation cascade, during which a receptor triggers a ligand-receptor mediated signal. Alterations in TNF activation can have profound effects on a multitude of cellular processes, such as the activation or inhibition of cell-specific responses, cell proliferation, inflammatory reactions, and cell death.

The interactions between TNF ligands and receptors may result in one-directional signaling (the interaction of the TNF receptor/ligand triggers a signaling cascade in the receptor only) or may result in bi-directional or reverse signaling. In the instances of bi-directional or reverse signaling, the interaction would not only activate the signaling cascade of the TNF receptor but would also trigger a signaling cascade in a cell bearing the TNF ligand. (S. Wiley et al., Jour. of Immun., 3235-39 (1996).) Thus, understanding the interaction between a TNF receptor and ligand may result in therapeutic treatments involving the inhibition or enhancement of either one or both of the TNF receptor activity or TNF ligand activity.

One member of the TNF receptor family is the transmembrane activator and CAML-interactor (TACI), a cell surface protein. The TACI protein has been isolated and is described in WO 98/39361. When activated, TACI stimulates the influx of calcium in lymphocytes and initiates the activation of a transcription factor through a combination of a $Ca^{2+}$-dependent pathway and a $Ca^{2+}$-independent pathway. Functions of TACI include controlling the response of lymphocytes to cancer and to foreign antigens in infections, graft rejection, and graft-vs.-host disease (GVHD). Furthermore, activation of lymphocyte signaling allows the positive selection of functional lymphocytes and negative selection against self-reactive clones. (WO 98/39361 at 15.)

TACI modulated signals are often activated by a extracellular ligand/receptor interaction, which then triggers an intracellular protein/protein interaction. One of the intracellular proteins which bind with the TACI protein has been identified. TACI interacts with the calcium-signal modulating cyclophilin ligand (CAML), a protein associated with the calcium pathway in lymphocytes. According to WO 98/39361, after the binding of the extracellular domain of TACI to an extracellular ligand, the cytoplasmic domain of TACI binds CAML, initiating a $Ca^{2+}$-dependent activation pathway, which includes the activation of the transcription factors, NF-AT, AP-1 and $NF_kB$, a factor implicated in the actions of other members of the TNF-receptor family. The regions for the interaction between TACI and CAML were defined as the cytoplasmic COOH-terminal 126 amino acids of TACI and the $NH_2$-terminal 201 amino acids of CAML. CAML's ability to act as a signaling intermediate was verified by the inhibition of TACI-induced activation of the transcription factor when blocked by a dominant-negative mutant. (Von Büllow, G. et al., Science, Vol. 278, p.138-141 (1997).)

Although this interaction between the cytoplasmic domain of TACI and CAML has been identified, little is known about the extracellular ligand with which TACI interacts to initiate the intracellular cascades. Given the important role TACI plays in signal transduction and given the potential therapies that may arise from the manipulation of the signaling cascades, there is a need in the art for the identification and understanding of the interaction of TACI with its signaling ligand. Further, there is a need for the development of assays and therapeutic methods using the interaction between TACI and its signaling ligand.

Another TNF protein that has been recently discovered is a ligand that has been designated Neutrokine α, which is described in WO 98/18921. Identical nucleotide and polypeptide sequences have also been disclosed as "TL5" in EP 0869180A1 and as "63954" in WO 98/27114. As a member of the TNF family, Neutrokine α polypeptides were described as useful in the treatment of tumor and tumor metastasis, infections by bacteria, virus and other parasites, immunodeficiencies, inflammatory disease, lymphadenopathy, autoimmune diseases, and GVHD. Neutrokine α was also described as useful to mediate cell activation and proliferation. Further, Neutrokine α polypeptides were described as primary mediators of immune regulation and inflammatory response. (WO 98/18921 at 11; EP 0869180A1 at 3.)

As Neutrokine α polypeptides may inhibit immune cell functions, the ligand was described as also having a variety of anti-inflammatory activities. (WO 98/18921 at 49.) Specifically, it was said that Neutrokine α polypeptides could be used as an anti-neovascularizing agent to treat solid tumors and for other non-cancer indications in which blood vessel proliferation is not wanted. (Id.) The polypeptides could also be employed to enhance host defenses against resistant chronic and acute infections and to inhibit T-cell proliferation by the inhibition of IL-2 biosynthesis. Finally, Neutrokine α polypeptides could also be used to stimulate wound healing and to treat other fibrotic disorders. (Id.)

As such activities may be modulated by the Neutrokine α polypeptides, knowledge of how the ligand functions would be of significant interest to the scientific community. WO 98/18921, EP 0869180A1 and WO 98/27114, however, fail to identify specific receptors with which Neutrokine α polypeptides bind. Identification of the related TNF receptor would allow those skilled in the art to identify antagonists which may then be used in therapies to treat the disorders associated with the Neutrokine α polypeptides. Thus, there is a need to greater understand this TNF ligand, identify the receptors with which it interacts, and determine how the interaction functions.

SUMMARY OF THE INVENTION

This invention aids in fulfilling these needs in the art by identifying a novel interaction between the extracellular domain of TACI and the Neutrokine α polypeptide (hereinafter referred to as TACI ligand (TACI-L)), and uses thereof. Specifically, the invention encompasses the identification of a novel interaction between TACI (SEQ. ID. NO.: 2) and TACI-L (SEQ. ID. NO.: 4).

The present invention provides a screening method for identifying molecules that enhance or inhibit the TACI/TACI-L interaction, or that prevent or inhibit dissociation of a complex formed by TACI and TACI-L. This screening method involves contacting a mixture of cells which express TACI and cells which express TACI-L with a candidate molecule, measuring cellular responses, and detecting the ability of the candidate molecule to inhibit or enhance the interaction between TACI and TACI-L or inhibit the dissociation of the complex formed by TACI and TACI-L. Successful inhibition indicates that the candidate molecule is an antagonist. Increased activation of TACI or TACI-L indicates that the candidate molecule is an agonist. The candidate molecules are preferably small molecules, antibodies or peptides.

In a further aspect of the present invention, a solid phase method may be used to identify small molecules which inhibit the interaction between TACI and TACI-L. Using this method, TACI may be bound and is placed in a mixture with labeled TACI-L. After contact, the amount of signal is measured. Diminished levels of signal indicate that the candidate molecule inhibited the interaction between TACI and TACI-L.

In a still further aspect, the present invention provides a screening method for identifying molecules which mimic the biological activity of the TACI/TACI-L interaction. This screening method involves adding a candidate molecule that binds to TACI or TACI-L to a biological assay and comparing the biological effect of the candidate molecule to the biological effect of TACI/TACI-L complex.

In yet a further aspect, the invention provides for a therapeutic use of agonists and antagonists of the TACI/TACI-L complex in the treatment of diseases modulated by the complex.

In still a further aspect, the invention provides for the antagonists and agonists of the TACI/TACI-L complex.

Finally, the invention relates to a kit to aid in the above determinations and uses.

BRIEF DESCRIPTION OF THE FIGURES

FIG. 1 shows the nucleotide (SEQ. ID. NO.:1) (FIG. 1a) and deduced amino acid (SEQ. ID. NO.:2)(FIG. 1b) sequences of the TACI protein.

FIG. 2 shows the nucleotide (SEQ. ID. NO.:3) (FIG. 2a) and deduced amino acid (SEQ. ID. NO.:4)(FIG. 2b) sequences of the TACI-L protein.

FIG. 4 shows the results of a plate binding assay capturing TACI-L in which the ligand is diluted 1:2.

FIG. 5 shows the results of a plate binding assay capturing TACI-L in which the ligand is diluted 1:5.

FIG. 6 shows the results of a plate binding assay capturing HuTACI/Fc.

DETAILED DESCRIPTION OF THE INVENTION

The terms "TACI" and "TACI protein" are used interchangeably to define the TNF receptor disclosed by WO 98/39361. TACI comprises an extracellular domain, a transmembrane domain, and a cytoplasmic domain.

"Fragments" of TACI encompass truncated amino acid sequences of the TACI protein that retain the biological ability to bind to TACI-L. An example of such a fragment is the extracellular domain. Such fragments are identified in WO 98/39361, which is incorporated in this application in its entirety. "Soluble TACI" includes truncated proteins that lack a functional transmembrane domain of the protein but retain the biological activity of binding to TACI-L. The soluble, extracellular domain can be used to inhibit cellular activation.

"Homologous analogs" of TACI include isolated nucleic acids of the TACI protein that are at least about 75% identical to SEQ.ID.NO.:1 and retain the biological activity of binding to TACI-L. Also contemplated by the term are embodiments in which a nucleic acid molecule comprises a sequence that is at least 80% identical, at least 90% identical, at least 95% identical, at least 98% identical, at least 99% identical, or at least 99.9% identical to SEQ.ID.NO.:1 and retain the biological activity of binding to TACI-L. Further included are nucleic acids which are at least 85% similar, at least 95% similar, or at least 99% similar to nucleic acids that encode the amino acids of the TACI protein, as described in SEQ. ID. NO.:2, and that maintain a binding affinity to TACI-L. Still further included are all substantially homologous analogs and allelic variations.

The percent identity and percent similar may be determined by visual inspection and mathematical calculation. Alternatively, the percent identity of two nucleic acid molecules can be determined by comparing their sequences using the GAP computer program, version 6.0 described by Devereux et al. (*Nucl. Acids Res.* 12:387, 1984) and available from the University of Wisconsin Genetics Computer Group (UWGCG). The preferred default parameters for the GAP program include: (1) a unary comparison matrix (containing a value of 1 for identities and 0 for non-identities), and the weighted comparison matrix of Gribskov and Burgess, *Nucl. Acids Res.* 14:6745, 1986, as described by Schwartz and Dayhoff, eds., *Atlas of Protein Sequence and Structure*, National Biomedical Research Foundation, pp. 353-358, 1979; (2) a penalty of 3.0 for each gap and an additional 0.10 penalty for each symbol in each gap; and (3) no penalty for end gaps. Other programs used by one skilled in the art of sequence comparison may also be used.

The terms "TACI-L" and "TACI ligand" are used interchangeably to define the member of the TNF ligand family disclosed by WO 98/18921. TACI-L is also disclosed as "TL5" in EP 0869180A1 and as "63954" in WO 98/27114. The full-length TACI-L comprises an extracellular domain, a transmembrane domain, and a cytoplasmic domain. Although the exact location of the extracellular, transmembrane, and cytoplasmic domains may differ slightly due to different analytical criteria for identifying the functional domains, the range of amino acids 1 to 46 generally represents the intracellular domain; amino acids 47 to 72 represent the transmembrane domain, and amino acids 73-285, the extracellular domain.

"Fragments" of TACI-L encompass truncated amino acids of the TACI-L protein that retain the biological ability to bind to TACI. An example of such a fragment is the extracellular domain of TACI-L, which binds TACI. Another example of a TACI-L fragment is amino acids 123-285 of the extracellular domain of the TACI ligand.

"Soluble TACI-L" includes truncated proteins that lack a functional transmembrane domain of the protein but retain the biological activity of binding to TACI. The soluble, extracellular domain can be used to inhibit cellular activation.

"Homologous analogs" of TACI-L include isolated nucleic acids of the TACI-L protein that are at least about 75% identical to SEQ.ID.NO.:3 and retain the biological ability to bind to TACI. Also contemplated by the term are embodiments in which a nucleic acid molecule comprises a sequence that is at least 80% identical, at least 90% identical, at least 95% identical, at least 98% identical, at least 99% identical, or at least 99.9% identical to SEQ.ID.NO.:3 and retain the biological ability to bind to TACI. Further included are nucleic acids which are at least 85% similar, at least 95% similar, or at least 99% similar to nucleic acids that encode the amino acids of TACI-L, as described in SEQ. ID. NO.:4 and that maintain a binding affinity to TACI. Still further included are all substantially homologous analogs and allelic variations.

Sequences are substantially homologous when at least 50% (preferably 60%, more preferably 65%, more preferably 75%, more preferably 85%, and most preferably 99%) of the nucleotides match over the defined length of the DNA sequences. Sequences which are substantially homologous can be identified by comparing the sequences using software known in the art or by the well-known Southern hybridization experiment. Substantially homologous analogs and allelic variations must maintain the same biological activity as the protein they are homologous to (e.g. bind to the same receptor or ligand).

The terms "TACI/TACI-L complex" or "TACI/TACI-L interaction" are used interchangeably and refer to the protein unit formed by the binding interaction of TACI to TACI-L.

The term "TACI/TACI-L fragment complex" includes the protein units formed in which at least one binding partner is either a fragment of TACI or TACI-L (e.g. the binding interaction of a TACI fragment to TACI-L, TACI to a TACI-L fragment, or a TACI fragment to a TACI-L fragment) or a homologous analog of TACI or TACI-L. The TACI/TACI-L fragment complex has the same biological activity, effects, and uses as the TACI/TACI-L complex, as described below. The term "biological activity" includes the binding of TACI to TACI-L or fragments thereof.

The term "biological effects" includes any cellular changes or effects which result from a protein-protein interaction or the interaction of a protein with an agonist or antagonist. Examples of a biological effect of the TACI/TACI-L complex include an increase or decrease in $Ca^{2+}$ ions resulting from a protein-protein interaction or the activation of the transcription factors, NF-AT, AP-1 and $NF_\kappa B$.

The TACI/TACI-L interaction is a protein-protein interaction. Protein-protein interactions can be observed and measured in binding assays using a variety of detection methodologies that include, but are not limited to, surface plasmon resonance (Biacore), radioimmune based assays, and fluorescence polarization binding assays. When performed in the presence of a test compound, the ability of the test compound to modulate (e.g. enhance or inhibit) the protein-protein binding affinity is measured. In one embodiment of the instant invention, the binding interaction between TACI and TACI-L occurs between the extracellular domain of the TACI protein and amino acids 123-285 of the extracellular domain of the TACI ligand.

The discovery of the interaction between TACI and TACI-L is described in detail in Examples 1-3. Briefly, a ligand expression construct was transfected into cells. The cells were incubated with TACI:Fc, bound with an antibody of TACI:Fc, and followed by a detecting agent. A soluble form of TACI-L was used in verifying the interaction and was produced by fusing a CMV leader sequence followed by a leucine zipper motif to the polypeptide. Other useful leader sequences include IgKappa and Growth Hormone. PCR was used to amplify the cDNA sequence which encodes the extracellular domain (amino acids 123-285) of TACI-L by using the restriction sites of specific oligonucleotides. CMV and leucine zipper sequences can be obtained by methods well known in the art, such as by PCR or by enzymatic digestion of previously cloned sequences. These fragments are ligated and inserted into the appropriate expression vector. (Smith et al., *Cell*, Vol. 73, 1349-1360.)

The interaction between TACI and TACI-L was further characterized by plate binding assays, as described in Examples 4 and 5. Plate binding assays were conducted capturing either the TACI protein or the TACI ligand. In each instance, a high affinity constant was obtained, demonstrating the close binding interaction between TACI and TACI-L.

The discovery and understanding of the interaction between the extracellular region of TACI and TACI-L can be used to determine potential agonists or antagonists and to further develop understanding of which cell types TACI-L acts upon. Assays may utilize the interaction between TACI-L and TACI to screen for potential inhibitors (antagonists) or enhancers (agonists) of activity associated with TACI-L molecules and identify candidate molecules which may serve as therapeutically active agents that enhance, inhibit or modulate the TACI/TACI-L complex. Potential antagonists to the TACI/TACI-L interaction may include small molecules, peptides, and antibodies that bind to and occupy the binding site of either TACI or TACI-L, causing them to be unavailable to bind to each other and therefore preventing normal biological activity. Other potential antagonists are antisense molecules which may hybridize to mRNA in vivo and block translation of the mRNA into the TACI-L protein. Potential agonists include small molecules, peptides and antibodies which bind to TACI or TACI-L and elicit the same or enhanced biological effects as those caused by the binding of TACI to TACI-L.

Small molecules are usually less than 10K molecular weight and possess a number of physiochemical and pharmacological properties to enhance cell penetration, resist degradation and prolong their physiological half-lives. (Gibbs, J., Pharmaceutical Research in Molecular Oncology, *Cell*, Vol. 79 (1994).) Antibodies, which include intact molecules as well as fragments such as Fab and F(ab')2 fragments, may be used to bind to and inhibit the TACI/TACI-L complex by blocking the commencement of the signaling cascade. Such activity by the antibodies could be useful in the treatment of Acute Respiratory Disease Syndrome (ARDS). (WO 98/18921 at 57.) It is preferable that the antibodies are humanized, and more preferable that the antibodies are human. The antibodies of the present invention may be prepared by any of a variety of well-known methods.

Antagonists may be employed to inhibit (antagonize) the interaction between TACI and TACI-L for therapeutic purposes to treat tumor and tumor metastasis and to combat various autoimmune diseases that may be modulated by the TACI/TACI-L complex, e.g. multiple sclerosis and diabetes, as well as other disorders, such as viral infection, rheumatoid arthritis, graft rejection, and IgE-mediated allergic reactions. A further disorder that may be treated by antagonists of the TACI/TACI-L interaction is inflammation mediated by the interaction. In general, the interaction may be used to study cellular processes associated with TNF-receptors such as immune regulation, cell proliferation, cell death, and inflammatory responses.

Specific screening methods are known in the art and many are extensively incorporated in high throughput test systems so that large numbers of test compounds can be screened within a short amount of time. The assays can be performed in a variety of formats, including protein-protein binding assays, biochemical screening assays, immunoassays, cell based assays, etc. These assay formats are well known in the art. The screening assays of the present invention are amenable to screening of chemical libraries and are suitable for the identification of small molecule drug candidates, antibodies, peptides.

A particular example of an assay for the identification of potential TACI antagonists is a competitive assay which combines TACI-L and a candidate molecule with TACI under the appropriate conditions for a competitive assay. Either TACI or TACI-L can be labeled so that the binding may be measured and the effectiveness of the antagonist judged. The label allows for detection by direct or indirect means. Direct means include, but are not limited to luminescence, radioactivity, optical or electron density. Indirect means include but are not limited to an enzyme or epitope tag.

By observing the effect that candidate molecules have on TACI/TACI-L complexes in various binding assays, on TACI/TACI-L mediated activity in functional tests, and in cell based screens, molecules that are potential therapeutics because they can modulate the TACI/TACI-L-binding interaction are identified. Such molecules either mimic the biological activity of the TACI/TACI-L complex, prevent the formation of the TACI/TACI-L complex or inhibit dissociation of the TACI/TACI-L complex already formed. Molecules preventing the interaction of TACI and TACI-L may be useful when enhancement of the immune system is desired. Antagonists of the dissociation of the TACI/TACI-L complex may be useful as immunosuppressants or antiinflammatory agents.

Molecules which inhibit or prevent the dissociation of the TACI/TACI-L complex can be identified by forming the complex in the absence of a candidate molecule, then adding the candidate molecule to the mixture, and changing the conditions so that, but for the presence of the candidate molecule, TACI would be released from the complex. The concentration of the free or bound TACI could then be measured and the dissociation constant of the complex could be determined and compared to a control.

Another method by which molecules which inhibit the interaction between TACI and TACI-L can be identified is the solid phase method, in which TACI is bound and placed in a medium with labeled TACI-L. After contact with a candidate molecule, the amount of signal produced by the interaction between TACI and TACI-L is measured. Diminished levels of signal, in comparison to a control, indicate that the candidate molecule inhibited the interaction between TACI and TACI-L. In a further embodiment of this method, TACI-L could be bound and TACI labeled.

Screening assays can further be designed to find molecules that mimic the biological activity of the TACI/TACI-L complex. Molecules which mimic the biological activity of the TACI/TACI-L complex may be useful for enhancing the interaction. To identify compounds for therapeutically active agents that mimic the biological activity of the TACI/TACI-L complex, it must first be determined whether a candidate molecule binds to TACI or TACI-L. A binding candidate molecule is added to a biological assay to determine its biological effects. The biological effects of the candidate molecule are then compared to the those of the TACI/TACI-L complex.

Thus, the present invention encompasses methods of screening candidate molecules for their ability to modulate TACI/TACI-L complexes and their ability to modulate activities mediated by TACI/TACI-L complexes. By observing the effect that the candidate molecule has on the known binding characteristics of TACI, TACI-L or fragments thereof, compounds that inhibit or enhance TACI/TACI-L binding can be identified. Typical candidate molecules are small molecules, antibodies, or peptides and may be part of extensive small molecule libraries developed for use in screening methods. In this context, the identification of small molecules which may interact with the TACI protein or the TACI ligand can be used to develop drugs that modulate the activation pathway and may allow physicians to treat distinct immune conditions without the negative side effects present in current therapies. For such therapeutic uses, the agonists or antagonists of the TACI/TACI-L complex identified can be administered through well-known means, including parenterally (subcutaneous, intramuscular, intravenous, intradermal, etc. injection) and with a suitable carrier. Formulations suitable for parenteral administration include aqueous and non-aqueous sterile injection solutions which may contain anti-oxidants, buffers, bacteriostats and solutes which render the formulation instonic with the blood of the recipient; and aqueous and non-aqueous sterile suspensions which may include suspending agents or thickening agents. The dosage will depend on the specific activity of the vaccine and can be readily determined by routine experimentation.

Generally, the conditions for an assay are conditions under which TACI and TACI-L would normally interact. In other words, for an assay to identify the inhibitor of the TACI//TACI-L interaction, the conditions would be such that, but for the candidate molecule, TACI and TACI-L would bind.

The following examples are offered by way of illustration, and not by way of limitation. Those skilled in the art will recognize that variations of the invention embodied in the examples can be made, especially in light of the teachings of the various references cited herein, the disclosures of which are incorporated by reference in their entirety.

EXAMPLE 1

Generation of TCI-FC

This Example describes a method of generating TACI-Fc. The cDNA sequence encoding the extracellular domain of TACI (amino acids 2-166) was amplified by PCR using a sense primer (5'-ataaccggtagtggcctgggccggagcaggcgag-3')

(SEQ. ID. NO. 6) and an antisense primer (5'-ataagatctgggctcgctgtagaccagggccacctgatc) (SEQ. ID. NO. 7). The amplified PCR fragment was digested with the appropriate restriction enzyme and then ligated into the mammalian expression vector pDC409, in-frame with the Ig kappa leader sequence at the 5' end and with the Fc portion of human IgG1 at the 3' end. The plasmid was transfected transiently in CV1/EBNA cells and the soluble protein TACI-FC was purified on a protein G-sepharose column. Protein concentration was determined by BCA analysis. Purity was assessed by SDS-PAGE analysis which, under reducing conditions, showed a single band at 42kDa.

EXAMPLE 2

Ligand Screening by Slide Binding Assay

This Example describes the method of a slide binding assay and demonstrates that the TACI-Fc protein interacted only with TACI-L. The purified TACI-Fc was used to screen against a cDNA panel containing known members of the ligand family (4-1BBL, CD40L, OX40L, CD27L, CD30L, RANKL, LT-alpha, LT-beta, LIGHT, TWEAK, FasL, TRAIL, proTNF and TACI-L). TACI-Fc was then bound to the slides by adding 2µg of the DNA encoding the members of the ligand family to a sterile tube and adding 75 µM choloroquine in transfection/growth medium to a final volume of 175 µl. 25 µl of DEAE-dextran (4mg/ml in PBS) was then added to the DNA solution and mixed.

The growth medium was aspirated from the slides and replaced with 3 ml of 75 µM choloroquine in the transfection/growth medium, followed by the addition of the DNA/DEAE-dextran mixture to the cells. The slides were rocked side-to-side and back-and-forth to distribute the precipitated DNA evenly. The slides were incubated at 37° C. for 4.5 hours.

The medium was aspirated and 3 ml 10% DMSO was added in the transfection/growth medium. After a 5 minute incubation period at room temperature, the medium was aspirated again and replaced with 3 ml fresh transfection/growth medium. The cells were then incubated at 37° C. for 2 days to allow for expression of the transfected cDNAs.

To screen for positive pools expressing the cell-bound protein, slides were incubated with TACI:Fc and then with a radioiodinated protein probe (labeled goat anti-human Fc F(ab')2) for 30 minutes at room temperature. The probe solution is then removed by aspiration and washed to remove the non-specifically bound probe. Finally, the slides were fixed by incubating each slide with 1 ml 2.5% glutaraldehyde in PBS for 30 minutes at room temperature to retain specifically bound label. The slides were then washed twice with 1 ml PBS and air-dried.

The dried slides were dipped in liquid photographic emulsion that has been warmed to 42° C., dried at room temperature and exposed for 2 days at room temperature before developing. The slides were examined at 25× magnification under bright-field illumination to detect cell types upon which the ligand is acting. TACI-Fc protein was found to bind only to cells transfected with the TACI-L. The ability of the TACI-FC to bind to CV1 expressing the TACI-L was also demonstrated by the well-known methods of flow cytometry.

EXAMPLE 3

Immunoprecipitation of Membrane—Associated TACI with the TACI-Ligand

Figure 1B:
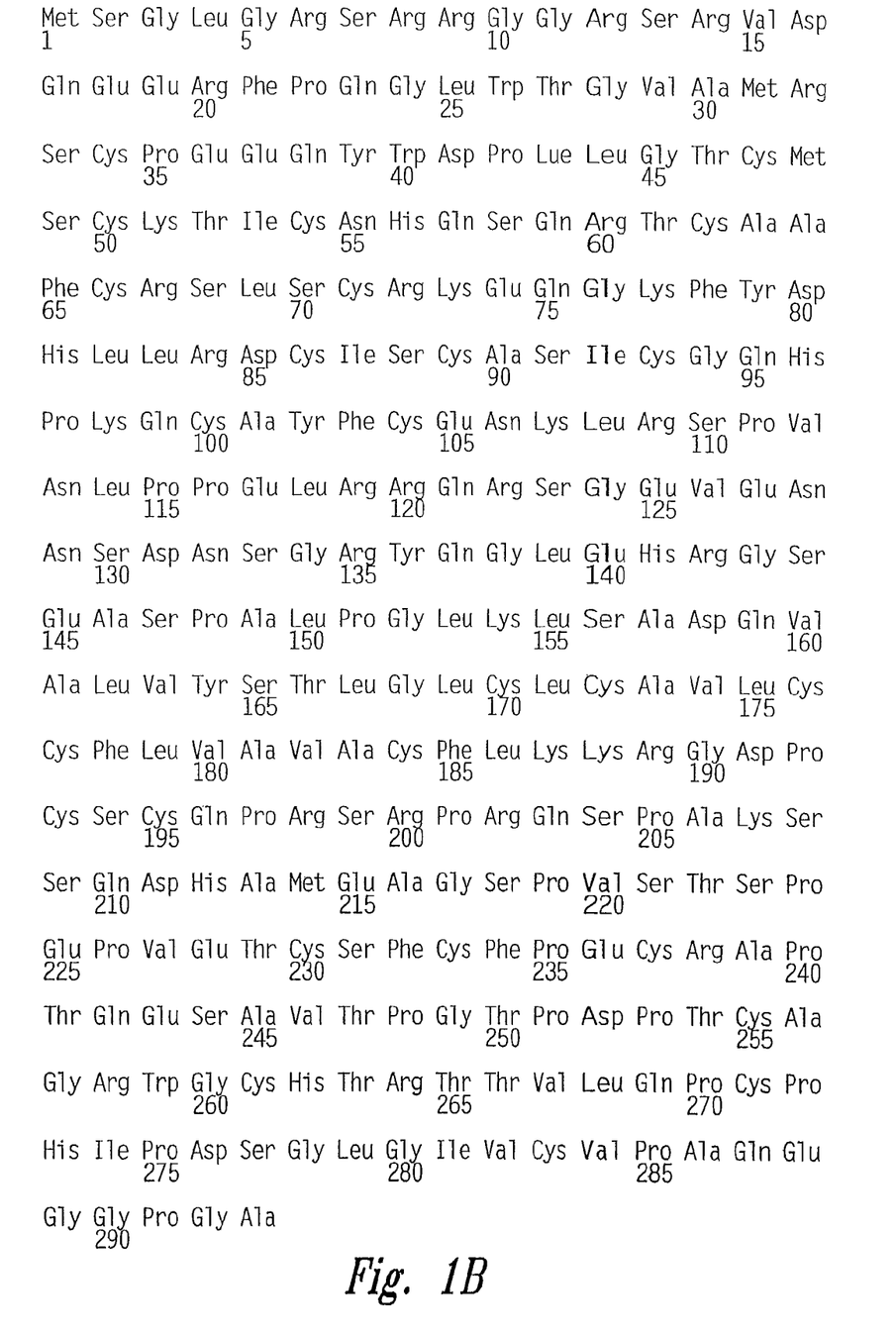
Figure 2A:
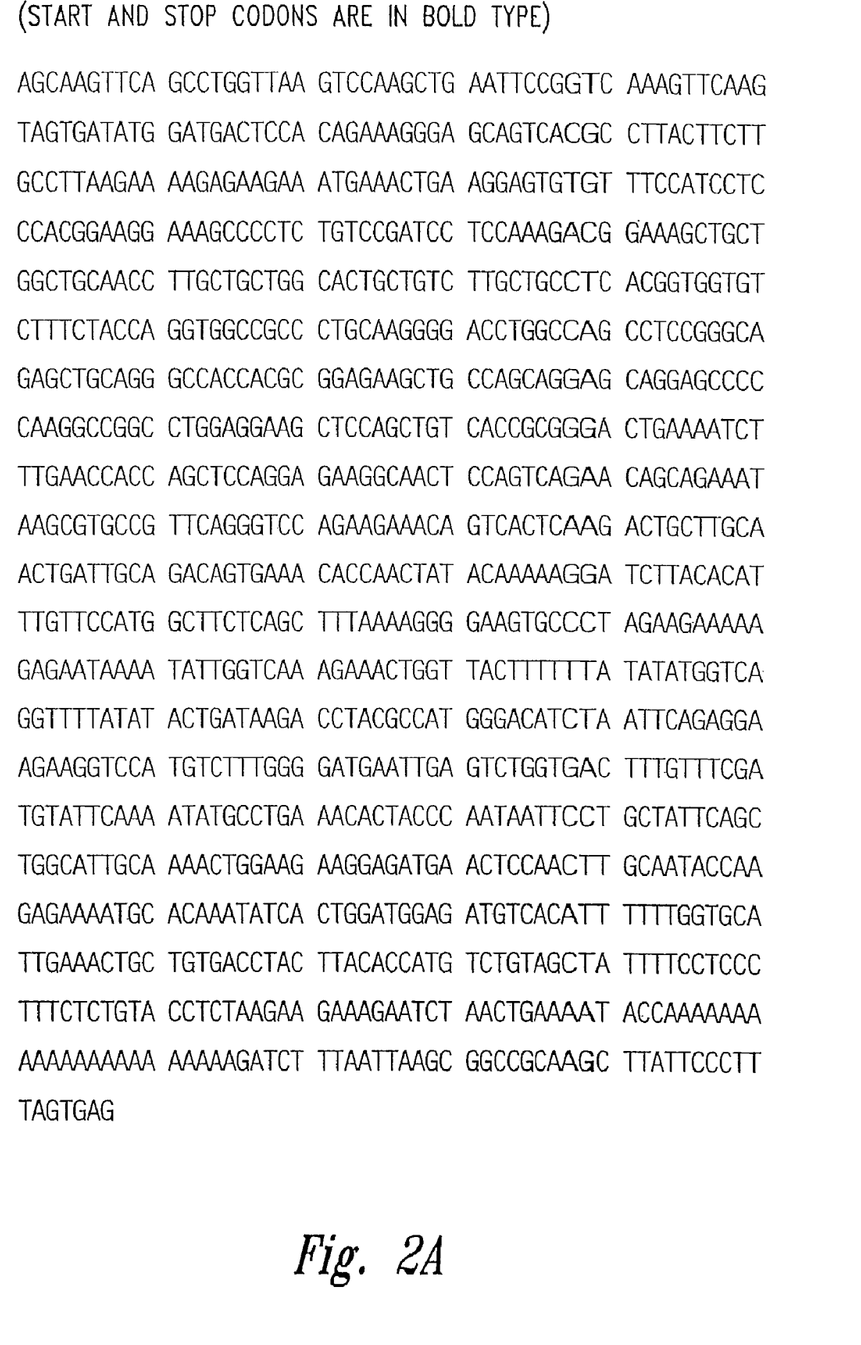
Figure 2B:
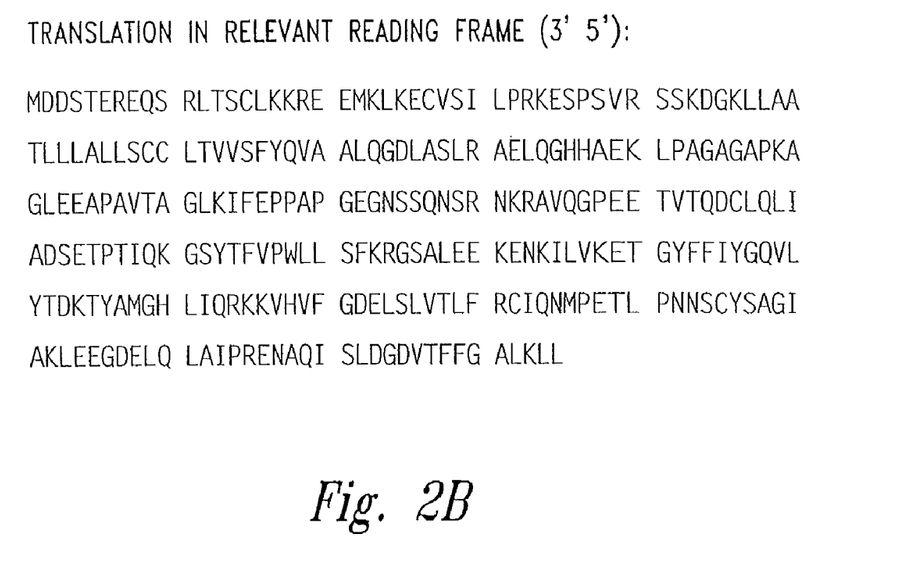
Figure 3:
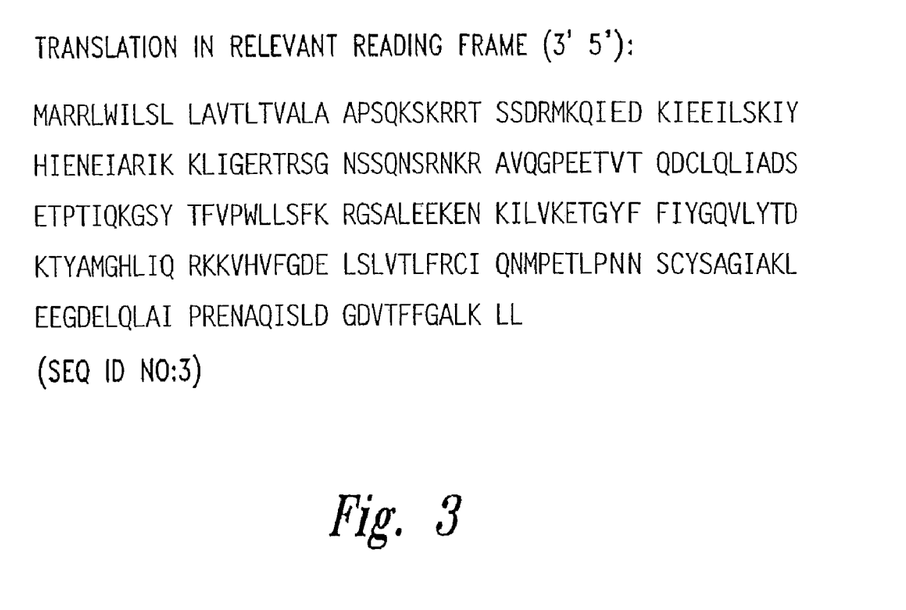
FIG. 3 shows the amino acid sequence of a polypeptide (SEQ. ID. NO.:5), in which a CMV leader followed by a leucine zipper motif is fused to the N-terminal region of the amino acid sequence of TACI-L.

This Example demonstrates the interaction between the TACI protein and TACI-L. CV1 cells were transfected with soluble TACI-L plasmid and the two day supernatant was harvested. CV1 cells were transfected with membrane associated TACI and metabolically labeled with 35S-CYS-MET two days post-transfection (labeled cell lysate). Supernatant containing TACI-L was used in immunoprecipitation experiments with labeled cell lysate. A specific band at 45 kDa which was consistent with the predicted size of TACI was obtained, as shown in FIG. 1. Thus, the interaction between the TACI protein and TACI-L was confirmed.

EXAMPLE 4

Plate Binding Assay Capturing TACI-L

This example further characterizes the interaction between TACI and TACI-L by conducting a plate binding assay and demonstrates the high affinity between the proteins. Equilibrium binding isotherms were determined in 96-well microtiter plates that had been coated with TACI-L COS expressed supernatants, captured through Leucine Zipper M15 antibody. Plates were incubated with 5 µg/ml LZ M15 in PBS for 4 hr at 4° C. After being washed 3 times with PBS, the plates were incubated with a 1:2 or 1:5 dilution of the COS expressing TACI supernatant in PBS/0.05% Tween 20 for 12 hours at 4° C. The plates were then washed for an additional 3 times with PBS and nonspecific binding sites were blocked with 300 µl/well of a binding media (RPMI 1640, 2.5% BSA, 20MM HEPES, 0.02% sodium azide pH 7.2) and 2.5% non-fat dried milk. The plates were incubated for 1 hour at room temperature and washed 3 times with PBS.

HuTACI/Fc was diluted to 2 µg/ml to the first well, and serial dilutions were performed against the binding media. Incubation occurred for 2 hours at 4° C. Plates were then washed 3 times with PBS. A final incubation occurred for 30 minutes at room temperature with 125 ng/ml 125-I goat anti-human F(ab')2. The goat anti-human F(ab')2 was labeled with 125-I using solid phase chloramine T analog (Iodogen; Pierce Chemical, Rockford, Ill.) to a specific radioactivity of 8.73e14 cpm/mmol. Nonspecific binding was determined in the presence of 1000-fold excess of unlabeled goat anti-human F(ab')2. Plates were washed 3 times in PBS and the specifically bound ligand was released with 50 mM citrate (pH 3.0) and then gamma counted. Data was processed as described (Dower et al., 1984).

Figure 4A:
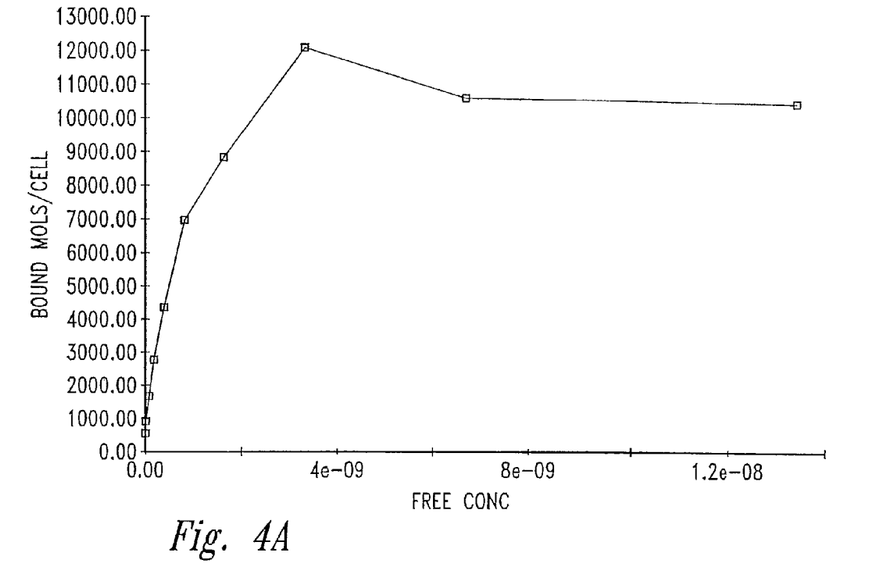
FIG. 4a demonstrates the results of the assay and shows the complete saturation of the receptor binding sites.
Figure 4B:
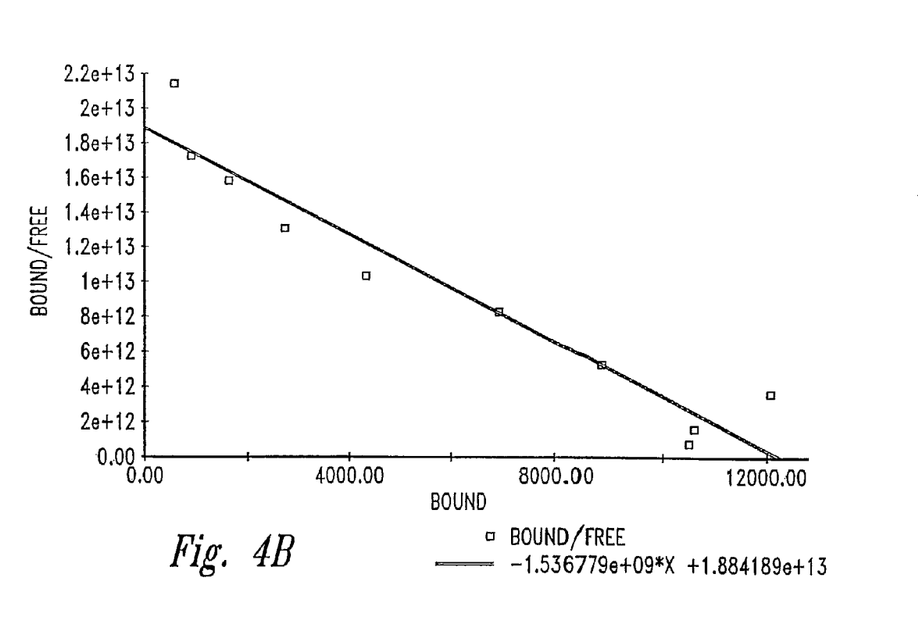
FIG. 4b, the Scatchard plot corresponding to FIG. 4a, demonstrates the actual number of sites that were bound. From these results, an affinity constant of $1.53 \times 10^{-9}$ can be generated.

FIG. 4a demonstrates the results of the assay using 1:2 dilution and shows the complete saturation of the receptor binding sites. FIG. 4b, the Scatchard graph corresponding to FIG. 4a, demonstrates the actual number of sites that were actually bound. From these results, the affinity constant of $1.53 \times 10^{-9}$ can be generated.

Figure 5A:
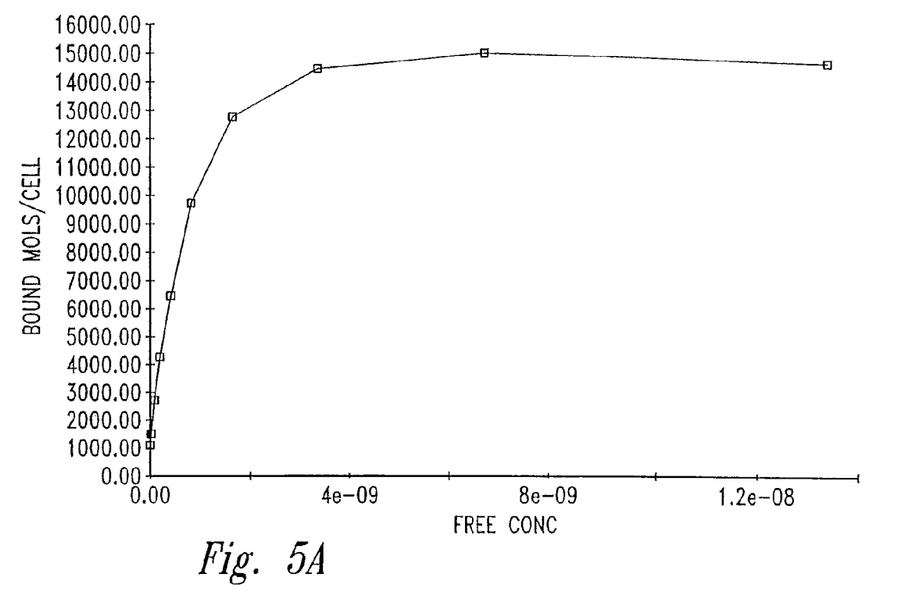
FIG. 5a demonstrates the results of the assay and shows the complete saturation of the receptor binding sites.
Figure 5B:
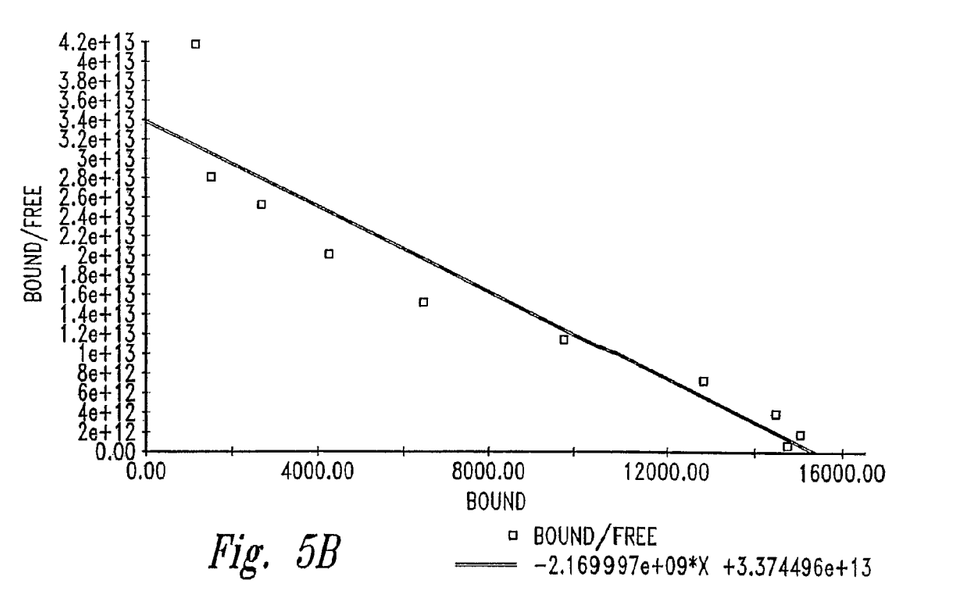
FIG. 5b, the Scatchard plot corresponding to FIG. 5a, demonstrates the actual number of sites that were bound. From these results, an affinity constant of $2.2 \times 10^{-9}$ can be generated.

FIG. 5a demonstrates the results of the assay using 1:5 dilution and shows the complete saturation of the receptor binding sites. FIG. 5b, the Scatchard graph corresponding to FIG. 5a, demonstrates the actual number of sites that were actually bound. From these results, the affinity constant of $2.2 \times 10^{-9}$ is shown.

EXAMPLE 5

Plate Binding Assay Capturing HuTACI/FC

This example also characterizes the interaction between TACI and TACI-L by use of a plate binding assay and further demonstrates the high affinity between the proteins. Equilibrium binding isotherms were determined in 96-well microtiter plates that had been coated with HuTACI/Fc, captured through goat anti-human Fc polyclonal antibody. Plates were incubated with 5 µg/ml goat anti-human FC in PBS for 4 hours at 4° C. After being washed 3 times with PBS, the plates were incubated with 0.1 µg/ml Fc chimera in PBS/0.05% Tween 20 for 12 hours at 4° C. and then washed for an additional 3 times with PBS. Nonspecific binding sites were blocked with 300 µl/well of a binding media (RPMI 1640, 2.5% BSA, 20MM HEPES, 0.02% sodium azide pH 7.2) and 2.5% non-fat dried milk. The plates were incubated for 1 hour at room temperature and then washed 3 times with PBS. TACI-L was expressed in COS cells and concentrated 10-fold.

TACI-L supernatant was diluted 1:10 to the first well, and serial dilutions were performed against the binding media. Incubation occurred for 2 hours at 4° C. Plates were then washed 3 times with PBS. A final incubation occurred for 30 minutes at room temperature with 125-I Leucine Zipper M15.

Leucine Zipper M15 (LZM15) was labeled with 125-I using solid phase chloramine T analog (Iodogen; Pierce Chemical, Rockford, Ill.) to a specific radioactivity of 8.73e14 cpm/mmol. Nonspecific binding was determined in the presence of 1000-fold excess of unlabeled LZM15. Plates were washed 3 times in PBS and specifically bound ligand was released with 50 mM citrate (pH 3.0) and then gamma counted. Data was processed as described (Dower et al., 1984).

Figure 6A:
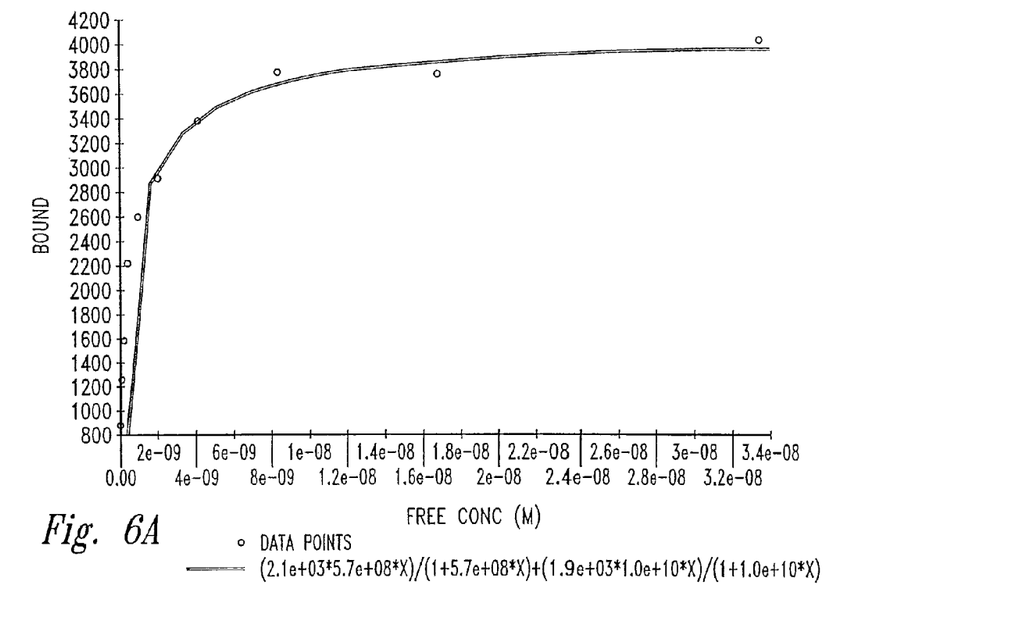
FIG. 6a graphs the complete saturation of the receptor binding sites.
Figure 6B:
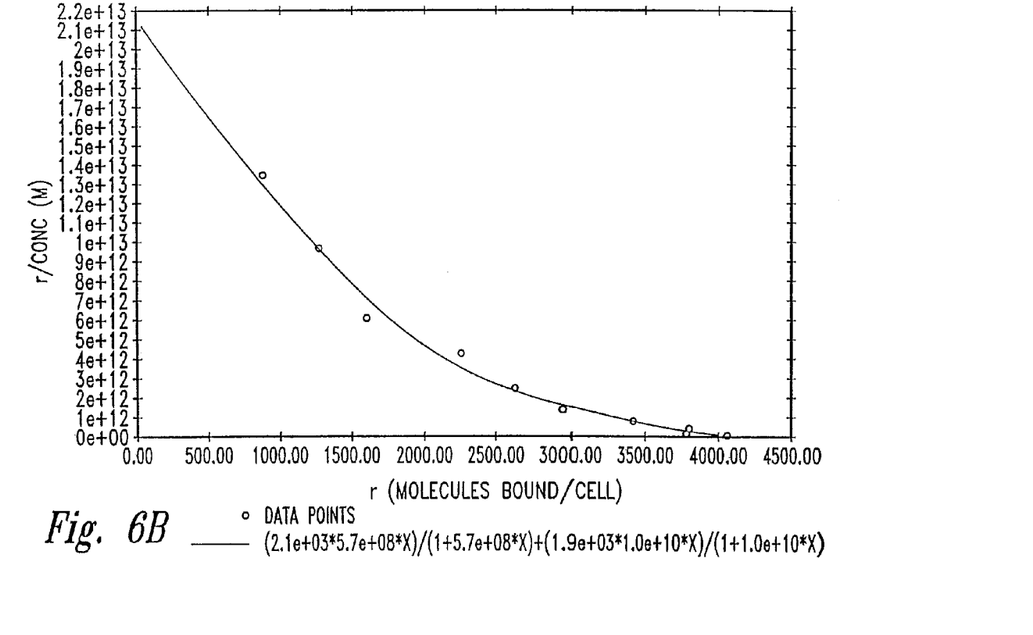
FIG. 6b, the Scatchard graph which corresponds to FIG. 6a, demonstrates the actual number of sites that were bound. The Scatchard plot of FIG. 6b demonstrates a curvilinear binding, with a low affinity constant of $5.7 \times 10^{-10}$ and a high affinity constant of $1.0 \times 10^{-10}$.

FIG. 6a demonstrates the complete saturation of the receptor binding sites. FIG. 6b, the Scatchard graph which corresponds to FIG. 6a, demonstrates the actual number of sites that were actually bound. The Scatchard graph of FIG. 6b demonstrates a curvilinear binding, with a low affinity constant of $5.7 \times 10^{-10}$ and a high affinity constant of $1.0 \times 10^{-10}$. FIG. 6b demonstrates that the majority of the binding occurred at an affinity constant between $2-3 \times 10^{-9}$.

The invention claimed is:

1. A method of inhibiting cellular activation through the binding of TACI (SEQ ID NO:2) to TACI-L (SEQ ID NO:4), comprising
   (a) exposing a cell expressing a TACI-L polypeptide of SEQ ID NO:4 to a TACI-Fc conjugate comprising amino acids 2-166 of SEQ ID NO:2 conjugated to a human Fc domain;
   (b) allowing the TACI-Fc conjugate to bind the TACI-L polypeptide; and
   (c) inhibiting the binding of an endogenous TACI polypeptide comprising SEQ ID NO:2 to the TACI-L polypeptide and thereby inhibiting the activation of the cell.

* * * * *